US008452545B2

(12) United States Patent (10) Patent No.: US 8,452,545 B2
Blasberg et al. (45) Date of Patent: May 28, 2013

(54) METHOD AND SYSTEM FOR DETERMINING THE DIFFERENCE BETWEEN PRE-PRANDIAL AND POST-PRANDIAL BLOOD GLUCOSE VALUES

(75) Inventors: Peter Blasberg, Weinheim (DE); Alfred Kloos, Unterhaching (DE); Matthias Koehler, Laudenbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 372 days.

(21) Appl. No.: 12/704,594

(22) Filed: Feb. 12, 2010

(65) Prior Publication Data

US 2010/0250144 A1 Sep. 30, 2010

(30) Foreign Application Priority Data

Mar. 30, 2009 (EP) ..................... 09004527

(51) Int. Cl.
*G01N 33/48* (2006.01)
*G01N 31/00* (2006.01)
*G06G 7/48* (2006.01)
*G06G 7/58* (2006.01)

(52) U.S. Cl.
USPC .................... 702/19; 702/22; 703/11; 703/12

(58) Field of Classification Search
None
See application file for complete search history.

(56) References Cited

U.S. PATENT DOCUMENTS

| 2007/0033074 A1 | 2/2007 | Nitzan et al. |
| 2007/0179352 A1 | 8/2007 | Randlov et al. |
| 2008/0071580 A1 | 3/2008 | Marcus et al. |
| 2008/0234943 A1 | 9/2008 | Ray et al. |

OTHER PUBLICATIONS

"Guideline for Management of Postmeal Glucose", International Diabetes Federation (IDF), ISBN 2-930229-48-9, Oct. 2007. Available at http://www.idf.org/webdata/docs/Guideline_PMG_final.pdf.
"Standards of Medical Care in Diabetes—2008", American Diabetes Association (ADA), Diabetes Care, vol. 31, Supp. 1, Jan. 2008. Available at http://care.diabetesjournals.org/content/31/Supplement_1/S12.full.pdf+html? maxtoshow=&HITS=10&hits=10&RESULTFORMAT=1&andorexacttitle=and&titleabstract=Standards+of+medical+Care&andorexacttitleabs=and& andorexactfulltext=and&searchid=1&FIRSTINDEX=0&sortspec=relevance&fdate=1/1/2007&tdate=4/30/2008&resourcetype=HWCIT.
Tshiananga, J.K. et al., "Reliability of self-recorded blood glucose data in patient logbooks compared with SMBG data saved in device memory and printed out with Accu-Chek Smart Printer", Diabetologia, Journal of the European Association for the Study of Diabetes, vol. 50, Suppl. 1, Sep. 2007, p. 1004.

*Primary Examiner* — Larry D Riggs, II
(74) *Attorney, Agent, or Firm* — Roche Diagnostics Operations, Inc.

(57) ABSTRACT

A method and system is disclosed that enables a less error-prone and preferably automatic assignment of pre-prandial and post-prandial blood glucose values associated with a meal to improve determining the difference between pre-prandial and post-prandial blood glucose measurements as follows. Blood glucose measurements are read and provided with a relative or absolute time mark and labeled as pre-prandial and reading out post-prandial blood glucose measurements provided with a relative or absolute time mark from the memory of a blood glucose measuring instrument. The chronological sequence of the blood glucose measurements labeled as pre-prandial are determined. The post-prandial blood glucose measurements that correspond to each of the pre-prandial blood glucose measurements are determined by applying a time selection criterion. The difference between corresponding pre-prandial and post-prandial blood glucose measurements is determined. The difference values are displayed that have improved diagnostic value.

9 Claims, 1 Drawing Sheet

Logbook

| | Date | 07:00-08:59 | 09:00-11:44 | 11:45-13:59 | 14:00-16:59 | 17:00-19:29 | 19:30-21:59 | 22:00-23:59 | 00:00-06:59 |
|---|---|---|---|---|---|---|---|---|---|
| Wednesday | 11.02.2009 | - | 202 ▪ | 137 □ | 186 ▪ | 103 □ | 209 ▪ | - | - |
| | 11.02.2009 | - | 99 □ | - | - | - | - | - | - |
| Tuesday | 10.02.2009 | - | 175 ▪ | 119 □ | 187 ▪ | 144 □ | 184 ▪ | - | - |
| | 10.02.2009 | - | 108 □ | - | - | - | - | - | - |
| Monday | 09.02.2009 | 117 □ | 198 ▪ | 81 ▪ | - | - | 225 ▪ | - | - |
| | 09.02.2009 | - | - | 114 □ | - | - | 124 □ | - | - |
| Sunday | 08.02.2009 | 117 □ | 207 ▪ | 124 □ | 178 ▪ | 117 □ | 198 ▪ | - | - |
| Saturday | 07.02.2009 | 110 □ | 223 ▪ | 65 □ | 94 ▪ | 97 □ | 202 ▪ | - | - |
| Friday | 06.02.2009 | 106 □ | 189 ▪ | 94 □ | 146 ▪ | 115 □ | 214 ▪ | - | - |
| Thursday | 05.02.2009 | 121 □ | 205 ▪ | 133 ▪ | - | 101 □ | 196 ▪ | - | - |
| | 05.02.2009 | - | - | 97 □ | - | - | - | - | - |
| Wednesday | 04.02.2009 | 124 □ | 198 ▪ | 175 ▪ | - | 114 □ | 225 ▪ | - | - |
| | 04.02.2009 | - | - | 92 □ | - | - | - | - | - |
| Tuesday | 03.02.2009 | - | 225 ▪ | 184 □ | 114 ▪ | 101 □ | 189 ▪ | - | - |
| | 03.02.2009 | - | 115 □ | - | - | - | - | - | - |
| Monday | 02.02.2009 | 119 □ | 249 ▪ | 90 □ | 171 ▪ | 99 □ | 204 ▪ | - | - |
| Sunday | 01.02.2009 | 117 □ | 252 ▪ | 141 □ | 135 ▪ | 153 □ | 213 ▪ | - | - |
| Saturday | 31.01.2009 | 121 □ | 227 ▪ | 112 □ | 106 ▪ | 105 □ | 274 ▪ | - | - |
| Friday | 30.01.2009 | 123 □ | 232 ▪ | 85 ▪ | - | 96 □ | 198 ▪ | - | - |
| | 30.01.2009 | - | - | 108 □ | - | - | - | - | - |
| Thursday | 29.01.2009 | - | 205 ▪ | 168 ▪ | - | 144 □ | 231 ▪ | - | - |
| | 29.01.2009 | - | 101 □ | 110 □ | - | - | - | - | - |
| n | | 10 | 18 | 19 | 9 | 13 | 15 | 0 | 0 |
| MBG | | 118 | 189 | 117 | 146 | 115 | 206 | - | - |
| SD | | 6 | 50 | 33 | 36 | 20 | 31 | - | - |
| n □ | | 14 | | 14 | | 14 | | 0 | |
| MBG □ | | 114 | | 113 | | 115 | | - | |
| SD □ | | 8 | | 28 | | 19 | | - | |
| n ▪ | | | 14 | | 14 | | 14 | | 0 |
| MBG ▪ | | | 213 | | 140 | | 212 | | - |
| SD ▪ | | | 22 | | 39 | | 23 | | - |
| n (▪-□) | | | 10 | | 11 | | 11 | | 0 |
| ΔBG (▪-□) | | | 95 | | 22 | | 98 | | - |

| | □ | ▪ | ΔBG (▪-□) |
|---|---|---|---|
| Evaluated results | 84 | 42 | 42 | 32 |
| Mean BG (MBG) | 151 mg/cL | 114 mg/cL | 188 mg/cL | 71 mg/cL |
| Standard Deviation (SD) | 51 mg/cL | 20 mg/cL | 45 mg/cL | 50 mg/cL |
| Maximum | 274 mg/cL | | | |
| Minimum | 65 mg/cL | | | |

| | | | |
|---|---|---|---|
| ▪ Above Target | H Hypo | ▪ Weekend | ○ Hypo Symptoms |
| ▪ Below Target | □ BG Before Meal | ▪ BG After Meal | |

METHOD AND SYSTEM FOR DETERMINING THE DIFFERENCE BETWEEN PRE-PRANDIAL AND POST-PRANDIAL BLOOD GLUCOSE VALUES

This application claims priority to European Patent Application No. EP 09004527.9 filed Mar. 30, 2009, which is hereby incorporated by reference.

FIELD

The invention concerns a method and system for determining the difference between pre-prandial and post-prandial blood glucose values.

BACKGROUND

The question of how meals influence the level of blood glucose (also referred to as blood sugar) in diabetics is of high medical relevance. This is reflected for example by the fact that professional medical associations such as the IDF (International Diabetes Foundation) or the ADA (American Diabetes Association) have published guidelines on this topic (see for example http://www.idf.org/webdata/docs/Guideline_PMG_final.pdf or http://care.diabetesjournal.org/cgi/reprint/31/Supplement_1/S12.

The ingestion of meals or carbohydrates is the most important influencing factor for an increase of blood glucose in type 1 and type 2 diabetes. Increased levels of blood glucose are the most important factor for late complications of diabetes such as kidney failure, blindness, myocardial infarction, amputations, etc. However, the determination of the meal-related increase in blood glucose for the individual in relation to the main meals has not been adequately addressed.

Experimental tests such as GCT (Glucose Challenge Test) or OGTT (Oral Glucose Tolerance Test) are methods for determining the increases in blood glucose in which the patient ingests a defined amount of glucose and the blood glucose is determined before and at defined times after the ingestion. These tests can only be carried out under defined conditions in professional facilities, and they are time-consuming and stressful for the patient. Furthermore, these tests are carried out generally without the effect of anti-diabetic therapeutic agents.

Of medical relevance and interest is the effect of various meals on the blood glucose under the typical medication of the patient. This can be used as a basis to determine whether the type of medication, and dose and time of administration are suitable for keeping post-prandial blood glucose increases within certain limits.

The self-measurement of blood glucose is in principle a very suitable method for quantifying the said effects. However, certain boundary conditions have to be adhered to and checked in order to ensure the validity of the measured values.

In this connection it is important to accurately assign blood glucose values to a meal. In particular a measurement must be carried out immediately before the meal, another measurement must be carried out within a certain time frame after the meal and typically between 1 and at most 2 hours after the meal. Furthermore, several pairs of measurements for different days at different meal-times or times of days should be present in order to make statistically sound statements about the changes in blood glucose at various meal-times.

Apart from the above-mentioned clinical tests GCT and OGTT, only the self-measurement of blood glucose values is available at present. The measured values can then for example be recorded in diabetes diaries. These diaries often have categories such as "before breakfast" and "after breakfast" in which the measured values are then recorded and can be examined by the doctor. However, it is known from the literature that a high percentage (>50%) of the manually recorded blood glucose values are incorrect and incomplete (cf. e.g. Reliability of self-recorded blood glucose data in patient logbooks compared with SMBG data saved in device memory and printed out with Accu-Chek Smart Printer; J. K. Tshiang Tshiananga, D. Franke, M. Luebker, C. Weber, K. Neeser, 43rd EASD (2007) Annual Meeting, Amsterdam). Moreover, it is not possible to ascertain whether the time criteria for the measurements have been correctly adhered to. Furthermore, an evaluation of several measurement events is difficult to carry out and equally susceptible to error.

As an alternative the blood glucose values can be read out of the memory of the blood glucose measuring instrument and analyzed with appropriate software programs. Some blood glucose measuring instruments also allow individual values to be labeled as pre-prandial or post-prandial (i.e. in this connection as "before" or "after" a meal).

These software evaluations are usually based on arranging the stored measurements in various meal classes on the basis of the time of measurement. If the meal class "before breakfast" is for example defined as 5:30 am to 8:00 am, a value measured at 5:32 am is automatically assigned to this meal class. In some cases technical solutions are offered in which a measurement can be directly assigned to a certain meal class depending on the time.

The majority of the available software programs calculate average blood glucose values and spread (e.g. standard deviation or range) for the various meal classes.

The disadvantage of the existing solutions is that the type of statistic treatment of the measured blood glucose values could lead to an erroneous interpretation of the meal-related blood glucose differences.

Calculation of the isolated statistics for the individual meal classes can easily lead to conclusions about the influence of meals on the basis of differences in means between the "before" and "after" values (i.e. the pre-prandial and post-prandial measurements). These can for example be misleading because the "before" measurements have been carried out on different days than the "after" measurements and differences between the values are not due to the ingested meals. Moreover, the fact that a correct chronological sequence of blood glucose measurements in relation to meal ingestion is necessary for a correct determination of the meal-related blood glucose change is usually disregarded.

SUMMARY

The present invention provides a method and system which enables a less error-prone and preferably automatic assignment of pre-prandial and post-prandial blood glucose values associated with a meal. This should improve the evaluation methods and the associated medical conclusions.

A pre-requirement for the method for determining meal-related changes in blood glucose values that is described in the following is the labeling of blood glucose values as "before" or "after" the meal. This labeling takes place in the blood glucose measuring instrument directly in connection with the blood glucose measurement. A large number of blood glucose measuring instruments that are currently commercially available allow this labeling by a corresponding input via operating buttons on the measuring instrument.

The blood glucose measurements stored in a blood glucose measuring instrument can now be furnished with a relative (i.e., e.g. determined by an internal time counter which for example determines the relative time since the manufacture or first start-up of the measuring instrument) or absolute (i.e., e.g. with date and time) time mark and transferred together with these flags which are also referred to as pre-prandial or post-prandial flagging to a suitable evaluation program. In this connection the program can run in the blood glucose measuring instrument itself or in another suitable instrument for data processing such as e.g. a computer, mobile telephone, PDA or suchlike.

In an alternative embodiment of the invention, it is possible either automatically or after query to interpret an unflagged value or a value which has been erroneously flagged as pre-prandial as a post-prandial flagged value within a certain, predefined time frame e.g. 1.5 h after a value flagged as pre-prandial. This value is then typically subsequently flagged as an "after" blood glucose measurement.

Meal-induced changes in blood glucose are determined as follows.

Starting with the oldest value the data are searched for values which bear the flag "before", i.e., are labeled as pre-prandial values.

Starting from the time of a found "before" value, a search is made within a certain time frame, typically of at least 60 minutes and at most 140 minutes after the "before" value, for blood glucose values with the flag "after". If several blood glucose values with an "after" flag are found in this time segment, one of the "after" values and preferably the highest found measurement is used for the subsequent calculation.

The difference ("after" minus "before") of the found pair is determined and typically stored under one of four time headings ("breakfast", "lunch", "dinner" as well as "evening/night").

The appropriate time heading is determined on the basis of the time of measurement of the "before" value. The time blocks (before/after breakfast, before/after lunch, before/after dinner as well as evening/night) can preferably be individually set.

If a before/after pair has been determined and stored, the search is typically continued for further pairs after the previously found pair (i.e. after the time of measurement of the previously found "after" value) until all values have been searched up to the most recent blood glucose measurement. Typically, the oldest blood glucose pair is determined and then the next oldest blood glucose pair is determined, and these steps are repeated until all blood glucose measurements have been taken into consideration.

Subsequently the number, the mean and the standard deviation is determined and outputted for all found pairs as well as for the said time blocks.

The method according to the invention ensures that blood glucose measurement pairs belonging to a particular meal are in each case compared with one another. This enables more reliable information to be obtained about the influence of individual meals on the blood glucose value and the effect of therapeutic measures (e.g. insulin administration by injection, pens or insulin pumps, oral intake of blood glucose lowering drugs).

BRIEF DESCRIPTION OF THE DRAWINGS

The invention is elucidated in more detail on the basis of the figure.

FIG. 1 shows an example of a form for displaying blood glucose measurement data on the basis of a report.

DETAILED DESCRIPTION

The blood glucose measurements determined before and after meals have been labeled by the user of the measuring system and are labeled in the report of FIG. 1 with empty squares (value determined before a meal) and filled squares (value determined after a meal). The actual measured data together with week day, date, time range and "before" and "after" label are shown in the upper table-like area of FIG. 1. In addition to general statistical values the table also shows the values for the number n of the "before" and "after" blood glucose measurements (i.e. the pre-prandial and post-prandial blood glucose measurements), their means (MBG denoting mean blood glucose value), standard deviations (SD) and the differences between associated pre-prandial and post-prandial blood glucose measurement pairs ($\Delta$BG) in the respective time blocks. A summary of the data for all measurements is shown in the section below. It is also apparent from this that when the method according to the invention is used not all post-prandial values belonging to pre-prandial measurements were found because the number of value pairs in the column $\Delta$BG is only 32, but 42 pre-prandial and 42 post-prandial values were measured.

The method and system according to the invention allow so-called meal excursions (i.e. the increase or decrease of the blood glucose value after the ingestion of meals) to be simply detected and depicted. This in turn allows a simplified and improved control of insulin therapy and optionally an adaptation of the dose and time of meal-related insulin doses and thus ultimately to an improvement of the therapy and a reduction or avoidance of late diabetic squeal.

Thus, embodiments of the method and system for determining the difference between pre-prandial and post-prandial blood glucose values are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A method for determining the difference between pre-prandial and post-prandial blood glucose measurements, comprising the steps:
   i) reading out blood glucose measurements provided with a relative or absolute time mark and labeled as pre-prandial and reading out other blood glucose measurements provided with a relative or absolute time mark from the memory of a blood glucose measuring instrument;
   ii) determining the chronological sequence of the blood glucose measurements labeled as pre-prandial;
   iii) determining the post-prandial blood glucose measurement from the other blood glucose measurements that pairs with each of the labeled pre-prandial blood glucose measurements by applying a time selection criterion;
   iv) determining difference values between corresponding pairs of pre-prandial and post-prandial blood glucose measurements; and
   v) displaying the difference values.

2. The method according to claim 1, wherein
   allocating to time categories corresponding to meals the blood glucose measurements and the difference between corresponding pre-prandial and post-prandial blood glucose measurements.

3. The method according to claim 2, wherein
   the allocation to the time categories is based on the time of the pre-prandial blood glucose measurement.

4. The method according to claim 1, wherein
   determining the chronological sequence of the blood glucose measurements labeled pre-prandial is carried out in ascending order starting with the oldest pre-prandial blood glucose measurement.

5. The method according to claim 1, wherein the time selection criteria is a time frame from 60 minutes to 140 minutes starting after the respective labeled pre-prandial blood glucose measurement is used to identify the post-prandial blood glucose measurement.

6. The method according to claim 1, wherein if several post-prandial blood glucose measurements are present which fulfill the time selection criterion, the highest blood glucose measurement is used to pair with the corresponding pre-prandial blood glucose measurement.

7. The method according to claim 1, wherein steps ii) and iii) proceed in such a manner that
starting with the oldest pre-prandial blood glucose measurement firstly the highest corresponding post-prandial blood glucose measurement is determined;
storing this oldest blood glucose measurement pair for further processing;
determining subsequently the next oldest pre-prandial blood glucose measurement and the highest corresponding post-prandial blood glucose measurement;
storing this next oldest blood glucose measurement pair for further processing; and
repeating these steps until all blood glucose measurements have been taken into consideration up to the most recent pre-prandial blood glucose measurement and, optionally, the highest corresponding post-prandial blood glucose measurement.

8. A system for determining the difference between pre-prandial and post-prandial blood glucose measurements, comprising:
a blood glucose measuring instrument,
a data processing device, and
a computer program having instructions that when executed carry out the following a method for determining the difference between pre-prandial and post-prandial blood glucose measurements,
i) reading out blood glucose measurements provided with a relative or absolute time mark and labeled as pre-prandial and reading out other blood glucose measurements provided with a relative or absolute time mark from the memory of a blood glucose measuring instrument;
ii) determining the chronological sequence of the blood glucose measurements labeled as pre-prandial;
iii) determining the post-prandial blood glucose measurement from the other blood glucose measurements that pairs with each of the labeled pre-prandial blood glucose measurements by applying a time selection criterion;
iv) determining difference values between corresponding pairs of pre-prandial and post-prandial blood glucose measurements; and
v) displaying the difference values.

9. A non-transitory computer program product for determining the difference between pre-prandial and post-prandial blood glucose measurements, comprising:
a non-transitory computer program having instructions that when executed carry out a method for determining the difference between pre-prandial and post-prandial blood glucose measurements,
i) reading out blood glucose measurements provided with a relative or absolute time mark and labeled as pre-prandial and reading out other blood glucose measurements provided with a relative or absolute time mark from the memory of a blood glucose measuring instrument;
ii) determining the chronological sequence of the blood glucose measurements labeled as pre-prandial;
iii) determining the post-prandial blood glucose measurement from the other blood glucose measurements that pairs with each of the labeled pre-prandial blood glucose measurements by applying a time selection criterion;
iv) determining difference values between corresponding pairs of pre-prandial and post-prandial blood glucose measurements; and
v) displaying the difference values.

* * * * *